(12) United States Patent
Auch et al.

(10) Patent No.: US 6,776,050 B2
(45) Date of Patent: Aug. 17, 2004

(54) SUPPORT FOR BENDING TEST OF FLEXIBLE SUBSTRATES

(75) Inventors: Mark Auch, Singapore (SG); Ewald Guenther, Singapore (SG); Chua Soo Jin, Singapore (SG); Chen Zhong, Singapore (SG)

(73) Assignees: Osrano Opto Semiconductors GmbH, Regensburg (DE); Institute of Materials Research and Engineering, Singapore (SG)

( * ) Notice: Subject to any disclaimer, the term of this patent is extended or adjusted under 35 U.S.C. 154(b) by 32 days.

(21) Appl. No.: 09/968,135

(22) Filed: Sep. 28, 2001

(65) Prior Publication Data

US 2003/0061885 A1 Apr. 3, 2003

(51) Int. Cl.[7] ................................................. G01N 3/20
(52) U.S. Cl. ............................. 73/849; 73/760; 73/777; 73/799
(58) Field of Search .......................... 73/777, 760, 799, 73/812, 849

(56) References Cited

U.S. PATENT DOCUMENTS

| | | | | |
|---|---|---|---|---|
| 4,656,384 A | * | 4/1987 | Magori | 310/334 |
| 5,505,093 A | * | 4/1996 | Giedd et al. | 73/774 |
| 6,156,623 A | * | 12/2000 | Hendrix et al. | 438/457 |
| 6,478,906 B1 | * | 11/2002 | Azdasht et al. | 156/73.1 |

* cited by examiner

*Primary Examiner*—Edward Lefkowitz
*Assistant Examiner*—Andre Allen
(74) *Attorney, Agent, or Firm*—Dexter Chin

(57) ABSTRACT

A support for facilitating the bending test of flexible substrates is disclosed. The support includes a plastic or adhesive plastic applied on the substrate to keep the shards together after breakage, thereby eliminating the process of collecting the shards and fitting them back together for failure analysis.

30 Claims, 2 Drawing Sheets

SUPPORT FOR BENDING TEST OF FLEXIBLE SUBSTRATES

FIELD OF THE INVENTION

The present invention relates generally to thin flexible substrates such as those used to fabricate flexible devices. More particularly, the invention relates to the stress (bending) testing of thin glass substrates.

BACKGROUND OF THE INVENTION

To access the flexibility of thin substrates, bending tests have to be performed. During these tests, the substrate is subjected to bending until it breaks. The shards have to be reconstructed for the analysis to determine the breaking behavior.

The shards are not held together but are scattered after the breakage and have to be collected and fitted back together. This process of reconstruction is time-consuming. Furthermore, it is not always possible to fit all the shards back to their original positions as the shards are small and numerous, and scatter randomly in many different directions.

As evidenced from the above discussion, it is desirable to facilitate the reconstruction process by providing a means to keep the shards together after breakage.

SUMMARY OF THE INVENTION

The invention relates generally to thin flexible substrates, such as those used in microelectronics, optoelectronics and display devices. In particular, the invention facilitates the stress testing of flexible substrates like thin glass substrates. The present invention can also be used to facilitate stress testing of non-flexible substrates like silicon chips, chips of compound semiconductors or wafers as well as glass.

In accordance with the invention, a support is provided to keep the shards of the substrate together after breakage. In one embodiment, the support comprises a plastic layer attached to one side of a substrate. Alternatively, the plastic layer can be applied to both sides of the substrate. The plastic layer can be laminated on the substrate with an adhesive. Using plastic layer which includes an adhesive or comprises adhesive properties can also be used. Such plastic layers are referred to as, for example, adhesive plastic layers. Alternatively, the plastic layer is deposited using deposition techniques such as spin-coating or spraying. Subsequently, the substrate with the support undergoes a bending test until it shows a failure.

The shards are kept together by the plastic layer after breakage, and it is no longer necessary to collect the small shards and fit them back together. Hence, a more precise and efficient failure analysis of the flexible substrate can be done.

PREFERRED EMBODIMENTS OF THE INVENTION

Figure 1:
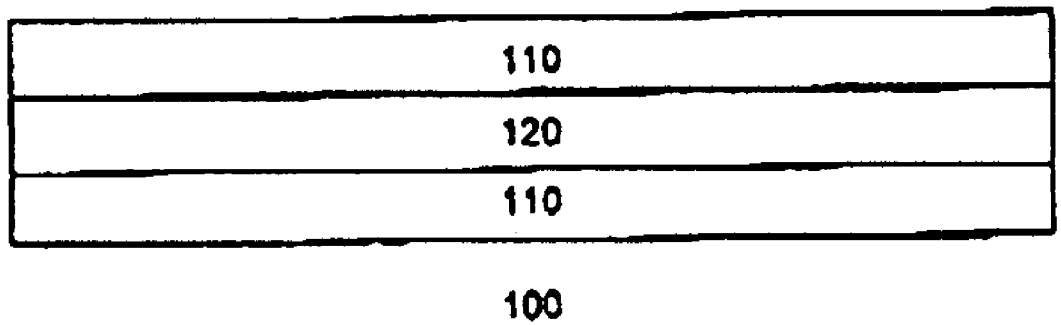
FIG. 1 shows an embodiment of the invention.
Figure 2:
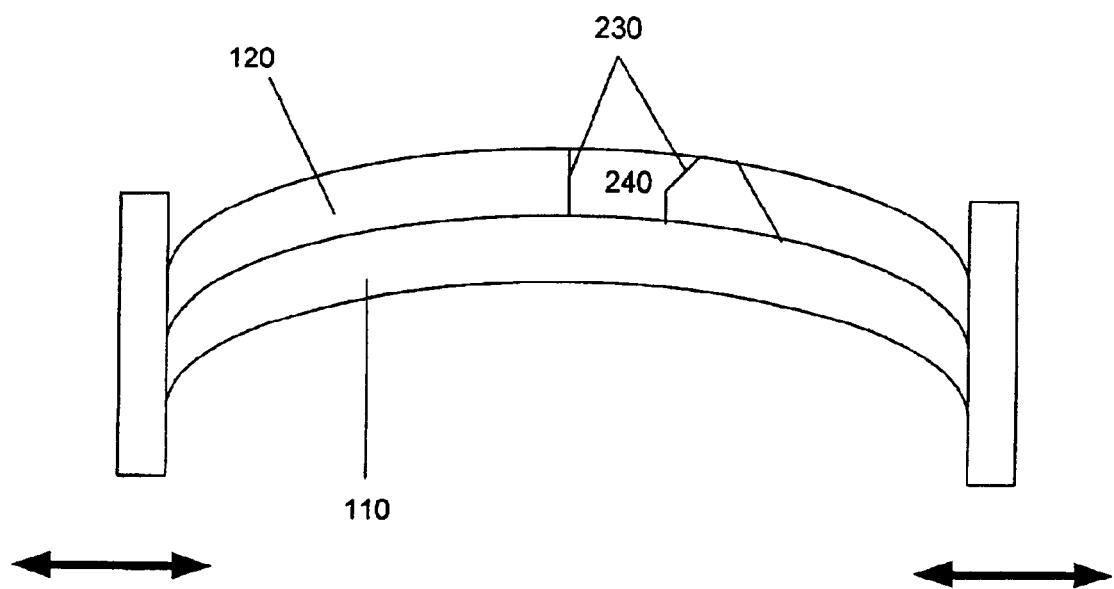
FIG. 2 shows the breaking test process

FIG. 1 shows one embodiment of the invention for facilitating stress testing of a substrate. A plastic layer 110 is attached to at least one side of a substrate 120. The substrate, for example, comprises glass. Other types of substrates, such as those formed from brittle or breakable materials or subjected to bending test, can also be used. The substrate is subjected to a bending or stress test, as shown in FIG. 2, resulting in fractures 230. The shard or shards 240 are held in place by the plastic layer after breakage.

In one embodiment, the plastic layer is attached on one side of the substrate. For substrates prepared with device layers, structures, or components on a top surface, the plastic layer preferably attached on the bottom surface of the substrate. Providing plastic layers on both surfaces can also be useful. In one embodiment, the plastic layer is attached to the surface of the substrate with an adhesive. Various types of adhesives, such as epoxy, can be used. Adhesive plastic layers processed with an adhesive or have adhesive properties can also be used. Other types of plastic layers which can be formed on and adhere to the substrate is also useful.

The plastic layer should have good adhesion to the substrate, a low Young's modulus and should not change the mechanical properties of tensile strength and bending modulus of the flexible substrate.

In one embodiment of the invention, the plastic layer is attached to the substrate by a laminating technique. Alternatively, the plastic layer is formed on the substrate using deposition techniques, such as spraying or spin-coating. Typically, the plastic layer is cross-linked after deposition. Other techniques for forming or providing the plastic sheet on the substrate are also useful. Subsequently, the substrate undergoes a bending or breaking test until it shows a failure. The fracture strain can easily be calculated from the given thickness, tensile strength and bending modulus of the substrate.

In a preferred embodiment of the invention, an adhesive plastic layer, for example the "ELEP HOLDER" wafer protection and holding tape from Nitto Denko, is deposited on one side of a thin glass substrate. The thin glass substrate, is about 50 $\mu$m thick. Another example of plastic layer that can be deposited on the substrate is the thermal release tape "REVALPHA" from Nitto Denko. In another embodiment, a laminating pouch film that, for example, is about 125 $\mu$m thick is applied onto the substrate by applying pressure and heat.

The glass substrate undergoes a bending test, during which it is bent until it breaks. The glass shards are held in place on the plastic sheet and can easily be identified.

While the invention has been particularly shown and described with reference to various embodiments, it will be recognized by those skilled in the art that modifications and changes may be made to the present invention without departing from the spirit and scope thereof. The scope of the invention should therefore be determined not with reference to the above description but with reference to the appended claims along with their full scope of equivalents.

What is claimed is:

1. An apparatus suitable for facilitating stress testing comprising:

a substrate having first and second major surfaces, wherein the substrate is formed from a breakable material; and a plastic layer having an adhesive on a first surface thereof, the plastic layer coating at least one of the major surfaces of the substrate, wherein the first surface of the plastic layer is in contact with the substrate, the adhesive on the plastic layer comprises sufficient adhesive property to maintain substantially all pieces of substrate in place on the plastic layer after substrate breakage from the stress testing.

2. The apparatus of claim 1 wherein the substrate comprises a flexible substrate.

3. The apparatus of claim 1 wherein the substrate comprises a non-flexible substrate.

4. The apparatus according of claim 1, 2 or 3 wherein the plastic layer coats a the first major surface of the substrate.

5. The apparatus of claim 1, 2 or 3 wherein the first and second major surfaces are coated with plastic layers.

6. The apparatus of claim 4 wherein the adhesive comprises epoxy.

7. The apparatus of claim 6 wherein the plastic layer comprises a material with a low Young's modulus to sufficiently avoid changing the mechanical properties of the substrate in order to reduce or minimize affecting the breaking behavior of the substrate.

8. The apparatus of claim 4 wherein the adhesive is processed with the plastic layer or is part of the plastic layer.

9. The apparatus of claim 8 wherein the adhesive comprises epoxy.

10. The apparatus of claim 9 wherein the plastic layer comprises a material with a low Young's modulus to sufficiently avoid changing the mechanical properties of the substrate in order to reduce or minimize affecting the breaking behavior of the substrate.

11. The apparatus of claim 5 wherein the adhesive comprises epoxy.

12. The apparatus of claim 11 wherein the plastic layer comprises a material with a low Young's modulus to sufficiently avoid changing the mechanical properties of the substrate in order to reduce or minimize affecting the breaking behavior of the substrate.

13. The apparatus of claim 5 wherein the adhesive is processed with the plastic layer or is part of the plastic layer.

14. The apparatus of claim 13 wherein the adhesive comprises epoxy.

15. A method for stress testing a substrate comprising:
providing a substrate having first and second major surfaces formed from a breakable material;
costing at least one of the major surfaces of the substrate with a plastic layer with an adhesive; and
applying stress to the substrate, wherein when the stress causes the substrate to break, wherein the adhesive comprises sufficient adhesive properties to maintain substantially all pieces of the substrate in place on the plastic layer.

16. The method of claim 15 wherein providing the substrate comprises providing a flexible substrate.

17. The method of claim 15 wherein providing the substrate comprises providing a non-flexible substrate.

18. The method of claim 15, 16 or 17 wherein coating comprises coating the first major surface of the substrate with the plastic layer.

19. The method of claim 18 wherein coating comprises coating using epoxy.

20. The method of claim 19 wherein coating comprises coating at least one of the major surfaces of the substrate with the plastic layer formed from a material with a low Young's modulus to sufficiently avoid changing the mechanical properties of the substrate in order to reduce or minimize affecting the breaking behavior of the substrate.

21. The method of claim 15, 16 or 17 wherein coating comprises coating the first and second major surfaces with plastic layers.

22. The method of claim 21 wherein the plastic layers comprise a material with a low Young's modulus to sufficiently avoid changing the mechanical properties of the substrate in order to reduce or minimize affecting the breaking behavior of the substrate.

23. The method of claim 22 wherein coating comprises coating by a laminating technique.

24. The method of claim 22 wherein coating comprises coating by deposition.

25. The method of claim 24 wherein coating by deposition comprises spraying.

26. The method of claim 25 further comprises cross-linking the plastic layer after deposition.

27. The method of claim 24 wherein coating by deposition comprises spin-coating.

28. The method of claim 27 further comprises cross-linking the plastic layer after deposition.

29. A substrate used for forming devices which is amenable for stress testing comprising:
the substrate, wherein the substrate includes first and second major surfaces and is formed from a breakable material; and
a plastic layer having an adhesive on a first surface thereof, the plastic layer coating at least one major surface of the substrate, wherein the first surface of the plastic in contact with the surface, the adhesive having sufficient adhesive properties to cause the plastic layer to maintain substantially all pieces of the substrate in place on the plastic layer after substrate breakage from the stress testing.

30. The substrate of claim 29 wherein the substrate comprises a flexible substrate and the adhesive is processed or is part of the plastic layer.

* * * * *

UNITED STATES PATENT AND TRADEMARK OFFICE
CERTIFICATE OF CORRECTION

PATENT NO. : 6,776,050 B2
DATED : August 17, 2004
INVENTOR(S) : Mark Auch et al.

It is certified that error appears in the above-identified patent and that said Letters Patent is hereby corrected as shown below:

Title page,
Item [73], Assignee, "Osrano" should read -- Osram --;

Column 3,
Line 4, "coats a the" should read -- coats the --;

Column 4,
Line 40, "surface" should read -- substrate --

Signed and Sealed this

Fifteenth Day of February, 2005

JON W. DUDAS
*Director of the United States Patent and Trademark Office*